(12) United States Patent
Ho

(10) Patent No.: US 7,243,657 B2
(45) Date of Patent: Jul. 17, 2007

(54) MULTI-FUNCTION PORTABLE ASHTRAY

(76) Inventor: Chen-Lung Ho, P.O. Box 44 - 2049, Taipei (TW) 10668

( * ) Notice: Subject to any disclaimer, the term of this patent is extended or adjusted under 35 U.S.C. 154(b) by 379 days.

(21) Appl. No.: 11/049,962

(22) Filed: Feb. 4, 2005

(65) Prior Publication Data
US 2006/0174900 A1  Aug. 10, 2006

(51) Int. Cl.
A24F 15/08 (2006.01)
A24F 15/18 (2006.01)
A24F 19/00 (2006.01)
A24F 19/10 (2006.01)

(52) U.S. Cl. .................. 131/240.1; 131/174; 131/231; 131/256; 131/257; 131/242; 220/911; 206/246; 206/496

(58) Field of Classification Search ............. 131/240.1, 131/174, 231, 256, 257, 242; 206/246, 496; 220/911
See application file for complete search history.

(56) References Cited

U.S. PATENT DOCUMENTS 2,498,330 A * 2/1950 Block .................. 131/256
2,653,614 A * 9/1953 Coffey ................. 131/174
4,897,033 A * 1/1990 Yang .................... 431/253

* cited by examiner

Primary Examiner—Steven P. Griffin
Assistant Examiner—Phu Nguyen

(57) ABSTRACT

A multi-function portable ashtray is used particularly to be carried on in a user's hand. The ashtray structure of this invention is used for collecting cigarette ashes and snipes and for avoiding a user to be scalded by cigarette as smoking. Furthermore, the other utility objects of this ashtray multi-function structure are keeping a user warm and distributing fragrance scent as a travel diffuser.

10 Claims, 10 Drawing Sheets

MULTI-FUNCTION PORTABLE ASHTRAY

BACKGROUND OF THE INVENTION

1. Field of the Invention

This invention relates to a multi-function portable ashtray and more particularly to be carried on in a user's hand for collection cigarette ashes and snipes, for avoiding a user to be scalded when smoking, as well as for keeping a user warm and for distributing fragrance scent.

2. Description of the Prior Art

The more the industry and commerce develop rapidly, the more the people compete keenly. So the mental pressures of present persons are greater and greater, the cigarette addicts are more and more many. Because some cigarette addicts discard cigarette ashes and spines to any place carelessly, the living environment is polluted gradually. Sometimes, smoking makes some cigarette addicts be scalded by a cigarette or even causes conflagrations; these problems hurt persons and cause a lot of troubles.

Furthermore, an existing portable ashtray can only collect cigarette ashes and spines without any other effect. Thus, most cigarette addicts are unwilling to carry it on and still discard cigarette ashes or spines carelessly. The environment is still dirty and messy and affects the living quality deeply. So, the existing portable ashtray does not make the designed function and utility yield well.

Therefore, considering of the defects and the inconvenience of the existing portable ashtray mentioned as above, this invention is created to increase the value and the range of substantial utility by inventor's professional knowledge and spirit of pursuing innovation and perfecting.

SUMMARY OF THE INVENTION

A multi-function portable ashtray comprises a trough, a cover, a shield, a pivot and a soft plug.

A barrel is set on one end of the trough. A groove is set beside the barrel. An inserting part is set on one end of the groove for fixing a burning fragrance, and a U-type part is set on another end. The U-type part joins a metal U-type piece by a spiral fixer for clipping a cigarette.

The cover is set over upon the trough. A cylinder is bulged on one side of the cover for inserting into the barrel. And an air vent is set on the cover corresponding to the groove for air flowing into the groove to help the burning of the cigarette or the fragrance.

A sticking part is set on one side of the shield for sticking into the air vent on the cover. And a clipping part is set on the opposite of the shield corresponding to the sticking part for clamping a brush. An aperture is set on the same end of the shield corresponding to the U-type part for tying an elastic rope of the soft plug. The soft plug is used to block up the U-type part for preventing the ashes of the cigarette or the fragrance from dropping.

The pivot is joining the cover with the trough and to make the cover be turned to open easily.

As the cover turns away, this invention can be used as an open style ashtray. As the cover is closed, this invention can be used as a portable ashtray, a cigarette smoking utensil, a travel diffuser, or a warm keeper.

The principal objects of this invention are: to reduce the problems of the environment pollution caused by cigarette ashes and spines as a portable ashtray, to avoid user be scalded as a pipe, to distribute fragrance scent as a travel diffuser, and to keep user warm by the temperature of burning fragrances, mugwort or cigarettes. Furthermore, it achieves the purpose of increasing utility by the design of a clipping brush for clean the accumulated ashes produced by cigarettes or fragrances easily.

DESCRIPTION OF THE PREFERRED EMBODIMENTS

Figure 1:
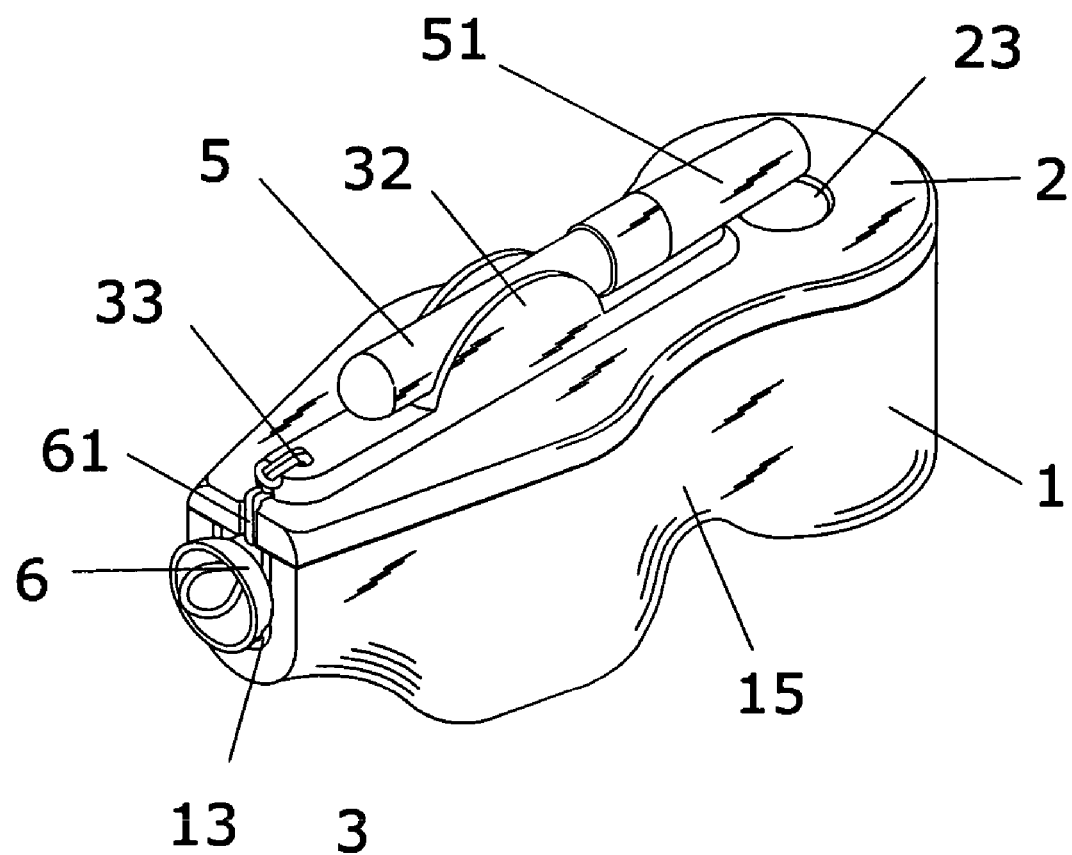
FIG. 1 is an assembly perspective view of a preferred embodiment of the present invention.
Figure 2:
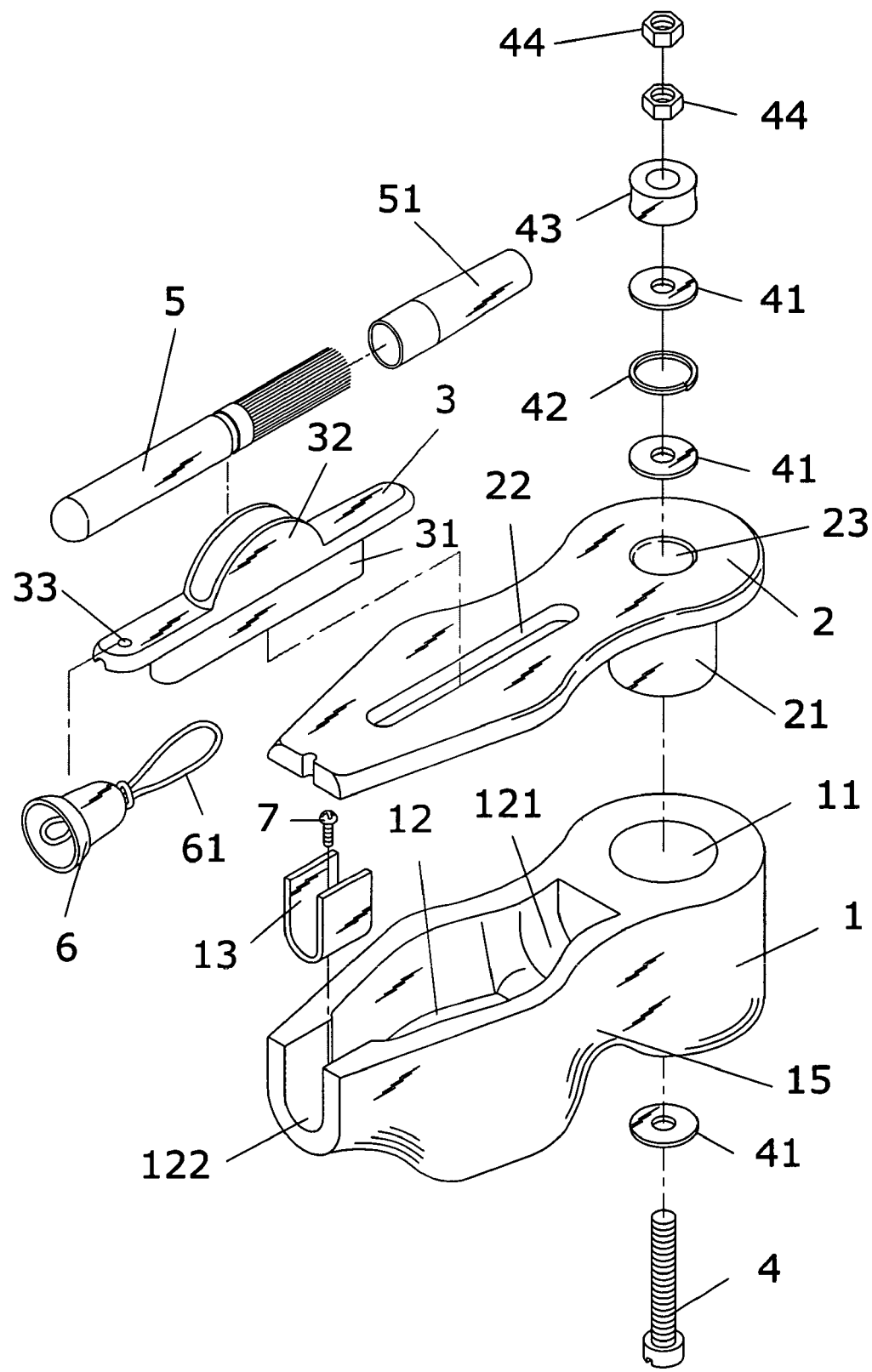
FIG. 2 is an exploded perspective view of a preferred embodiment of the present invention.
Figure 3:
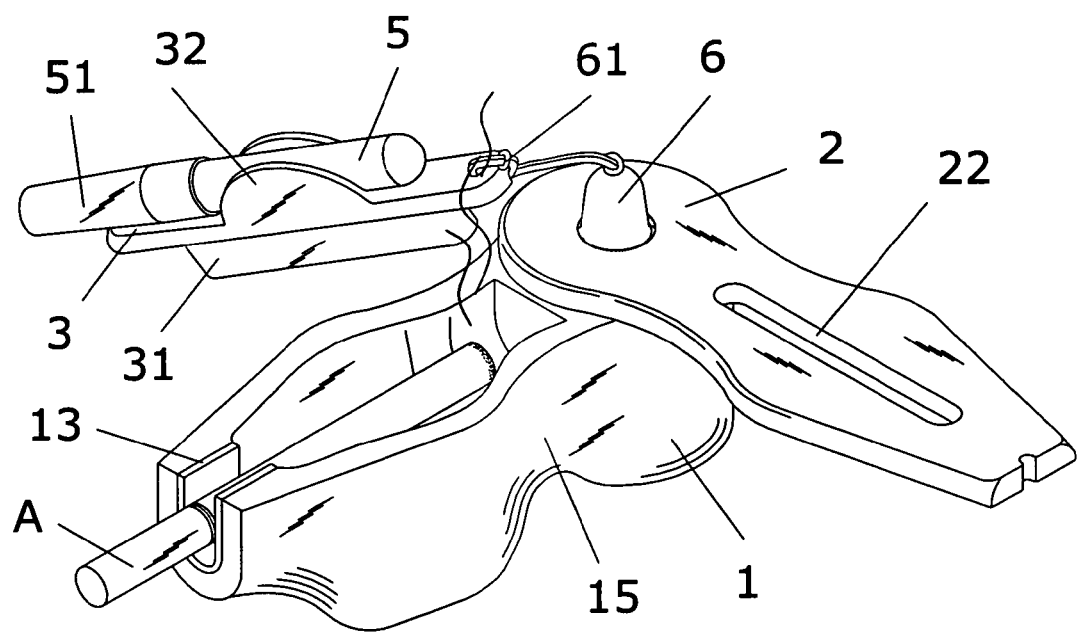
FIG. 3 illustrates the preferred embodiment of the present invention of FIG. 1 in an operating position as an ashtray.
Figure 4:
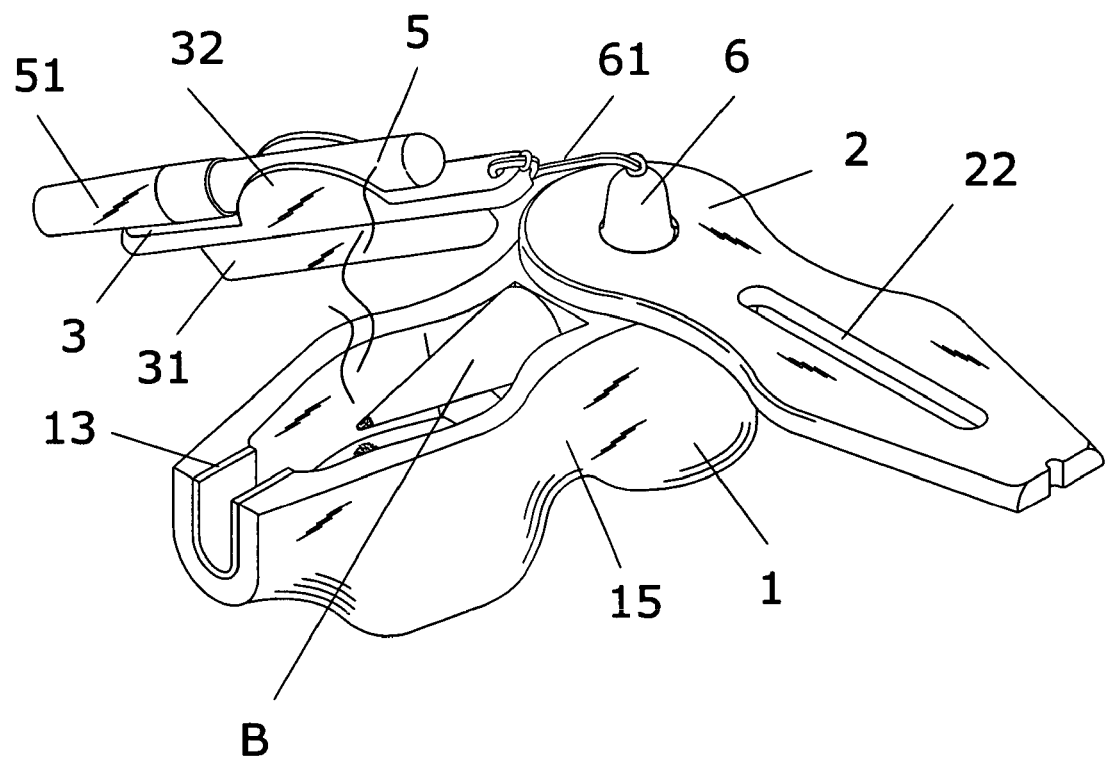
FIG. 4 illustrates the preferred embodiment of the present invention of FIG. 1 in an operating position as a travel diffuser.
Figure 5A:
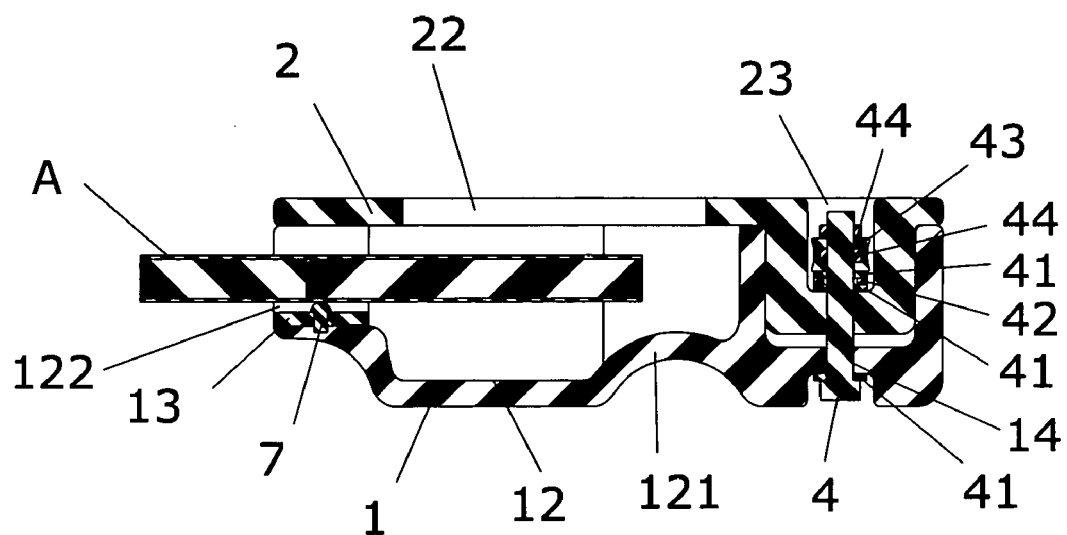
FIG. 5A is a cross-sectional view of the preferred embodiment of the present invention in an operating position as a smoking utensil.
Figure 5B:
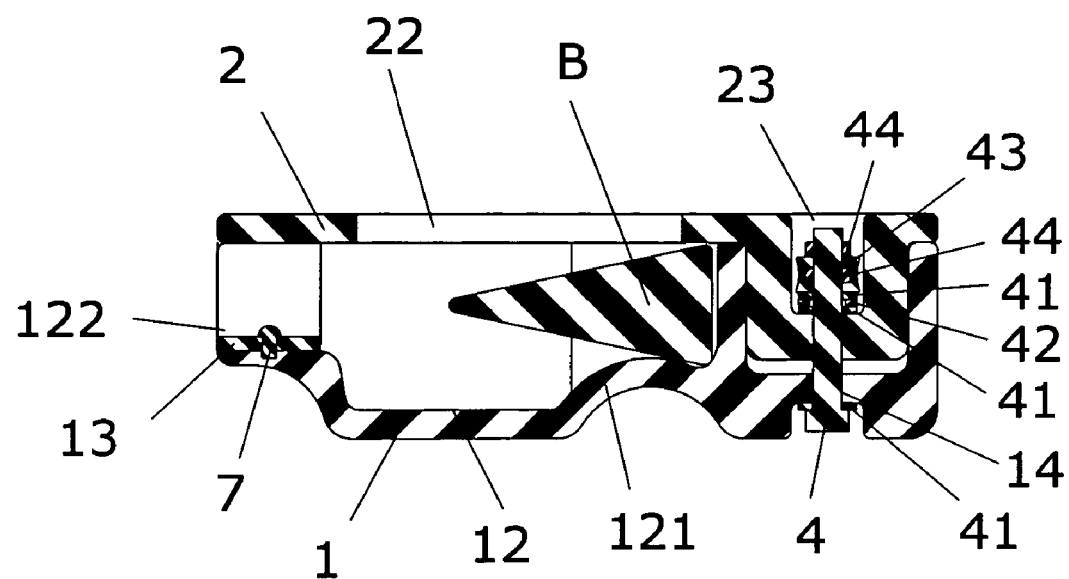
FIG. 5B is a cross-sectional view of the preferred embodiment of the present invention in an operating position as a travel diffuser.

This invention comprises a trough 1, a cover 2, a shield 3, a pivot 4, a brush 5 and a soft plug 6.

Referring to FIGS. 1, 2, 5A and 5B, a barrel 11 is set on one end of the trough 1 and a hole 14 is penetrated from the opposite side of the trough 1 corresponding to the barrel 11. A groove 12 is set hollowly beside the barrel 11. An inserting part 121 is set on one end of the groove 12 for fixing a burning fragrance B and a U-type part 122 is set on another end. The U-type part 122 joins a metal U-type piece 13 by a spiral fixer 7 for putting a cigarette A in order to avoid the burning cigarette A ruining the U-type part 122.

The cover 2 is set over upon the trough 1. A cylinder 21 is bulged on one side of the cover 2 for inserting into the barrel 11. An opening 23 is set on the cylinder 21. And an air vent 22 is set on the cover 2 corresponding to the groove 12 for air flowing into the groove 12 to help the burning of the cigarette A or the fragrance B.

A sticking part 31 is set on one side of the shield 3 for sticking into the air vent 22 on the cover 2. And a clipping part 32 is set on the opposite of the shield 3 corresponding to the sticking part 31 for clamping the brush 5. An aperture 33 is set on the same end of the shield 3 corresponding to the U-type part 122 for tying an elastic rope 61 of the soft plug 6. The soft plug 6 is used to block up the U-type part 122 for preventing the ashes of the cigarette A or the fragrance B from dropping.

The pivot 4 is penetrating to the cover 2 from the hole 14 into the opening 23 to make the cover 2 be turned to open easily. And three spacers 41, an elastic washer 42, a rubber plug 43 and two nuts 44 are set sequentially on the pivot 4 for joining the cover 2 tightly with the trough 1.

In addition, the opening 23 can be blocked by the soft plug 6, and a sheath 51 can be put on the brush 5 for keeping the brush 5 clean. And a holding part 15 is set on either opposite side of the trough 1 for preventing the user's hand from scalding as smoking. Moreover, as the soft plug 6 blocks in the U-type part 122, the elastic rope 61 tied on both the shield 3 and the soft plug 6 can avoid the shield 3 dropped out from the air vent 22.

About the assembly of this invention, the cylinder 21 of the cover 2 inserts into the barrel 11 of the trough 1. The pivot 4 is penetrated through the spacer 41 into the opening 23 from the hole 14. Then, the spacer 41, the elastic washer 42, the spacer 41, the rubber plug 43 and the nut 44 are set sequentially on the end of the pivot 4 in the opening 23 for joining the trough 1 and the cover 2 by fixing the nut 44 and also to make sure that the cover 2 can be turned to open. The sticking part 31 of the shield 3 sticks into the air vent 22 to make the shield 3 lay over the cover 2. And the soft plug 6 blocks the U-type part 122. After this, the brush 5 puts on the sheath 51 and then is clamped in the clipping part 32 of the shield 3.

Referring FIGS. 3, 4, 5A and 5B, the shield 3 is open first, then the soft plug 6 is rested in the opening 23 for preventing the shield 3 from dropping or missing. As the cover 2 turns away, this invention can be used as an open style ashtray for the burning cigarette A or as an open style diffuser for the burning fragrance B. As the cover 2 is closed, the air vent 22 on the cover 2 can provide air for the burning cigarette A or the burning fragrance B put in the groove 12. During winter, this invention can also be used as a warm keeper by the temperature produced by the burning cigarette A or the burning fragrance B. Furthermore, this invention can be used as a portable travel diffuser when the burning material on the groove 12 is the fragrance B.

Figure 6:
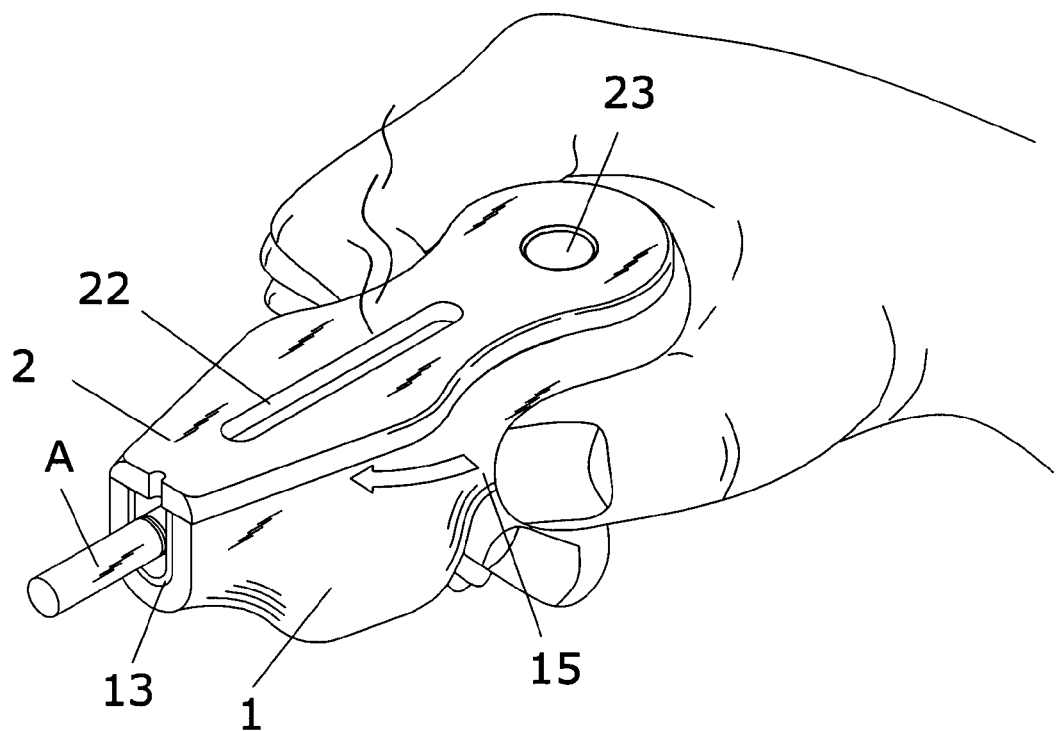
FIG. 6 is an assembly perspective view of FIG. 5A.
Figure 7:
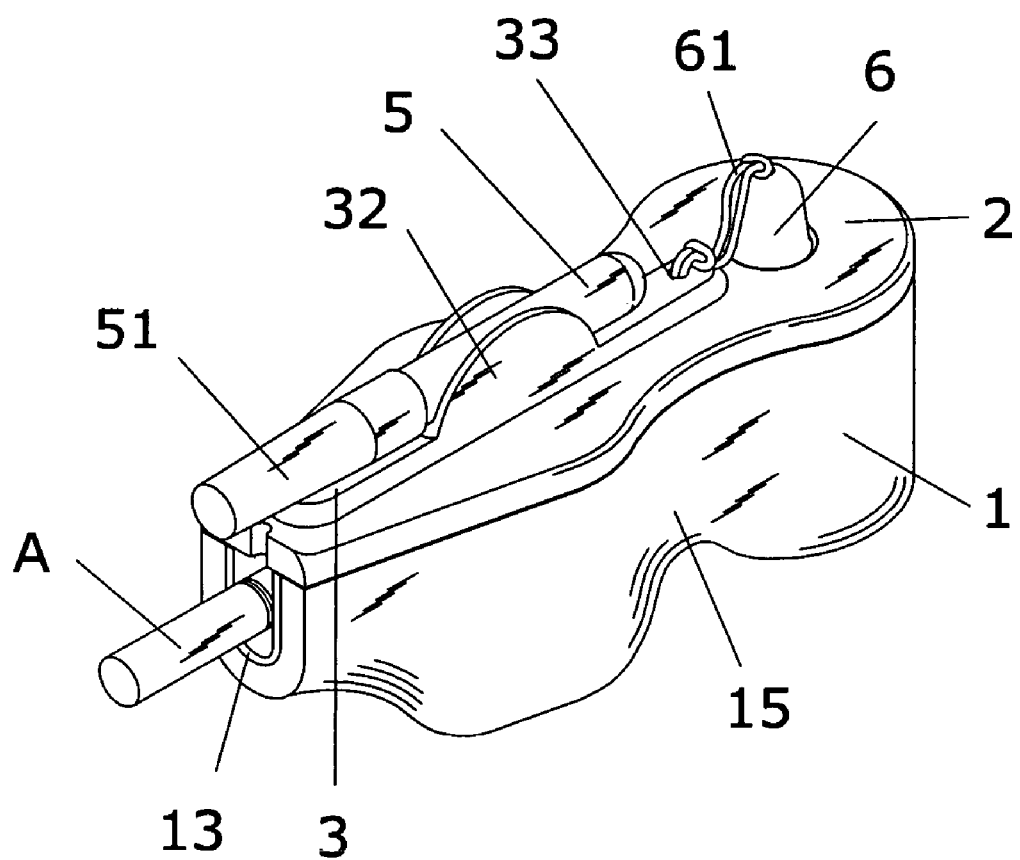
FIG. 7 is an assembly perspective view of FIG. 3.

Referring to FIG. 6, the cigarette A is lighted and is put in the groove 12 (unshown), and then the cover 2 is closed. A user can hold this invention as a smoking utensil which means to smoke the cigarette A directly. All the ashes and spines of the cigarette A are leaved in this ashtray. This achieves the purposes of reducing the environment pollution caused by ashes as well as spines of the cigarette A and of preventing a user from being scalded. Referring to FIG. 7, the shield 3 is set back into the air vent 22 to prevent the cigarette A ashes from dropping and to make the burning cigarette A or the burning fragrance B (unshown) be extinguished because of lacking oxygen. This also accomplishes the purpose of avoiding a conflagration.

Figure 8:
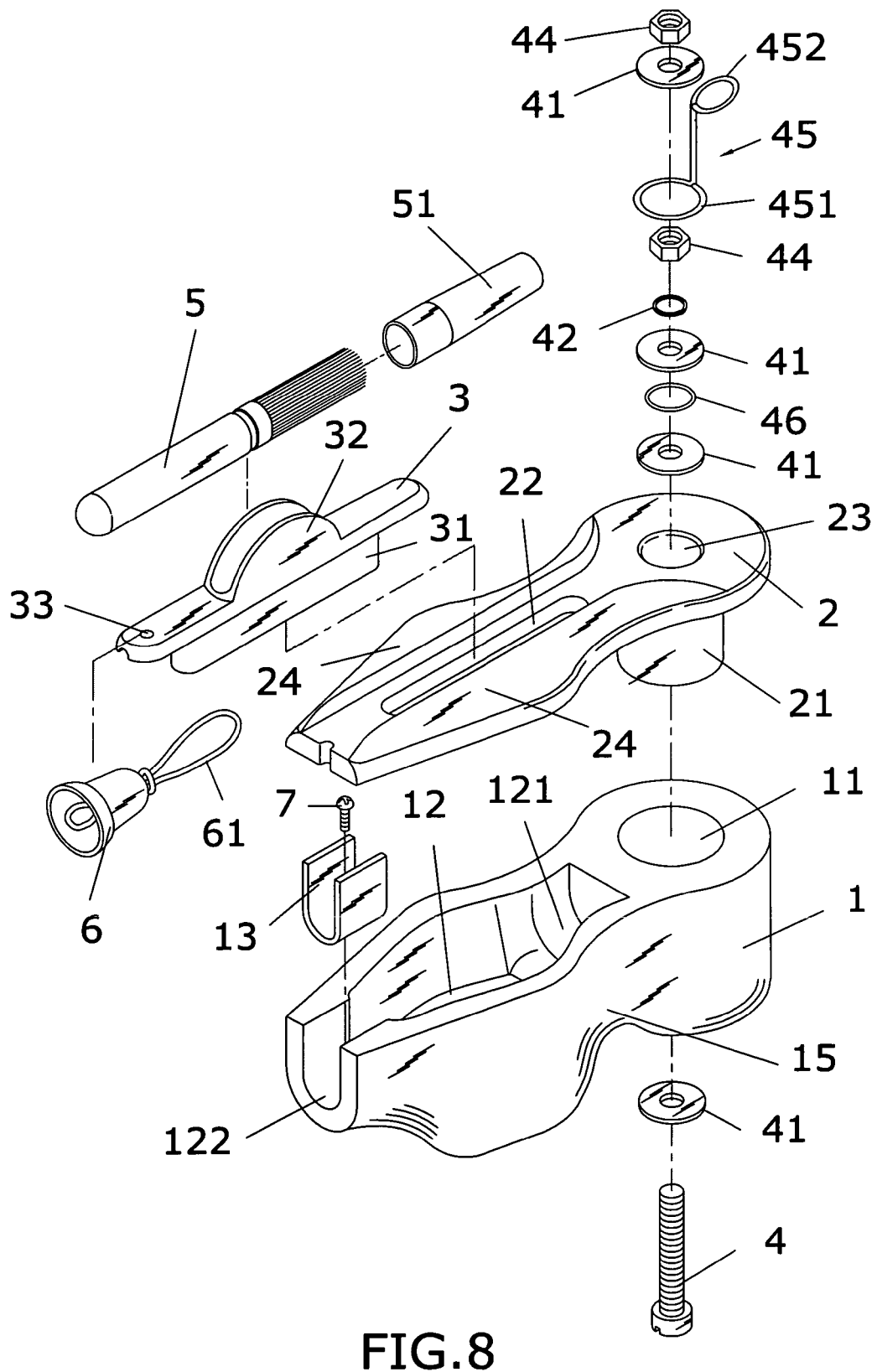
FIG. 8 is an assembly perspective view of the second preferred embodiment of the present invention.
Figure 9:
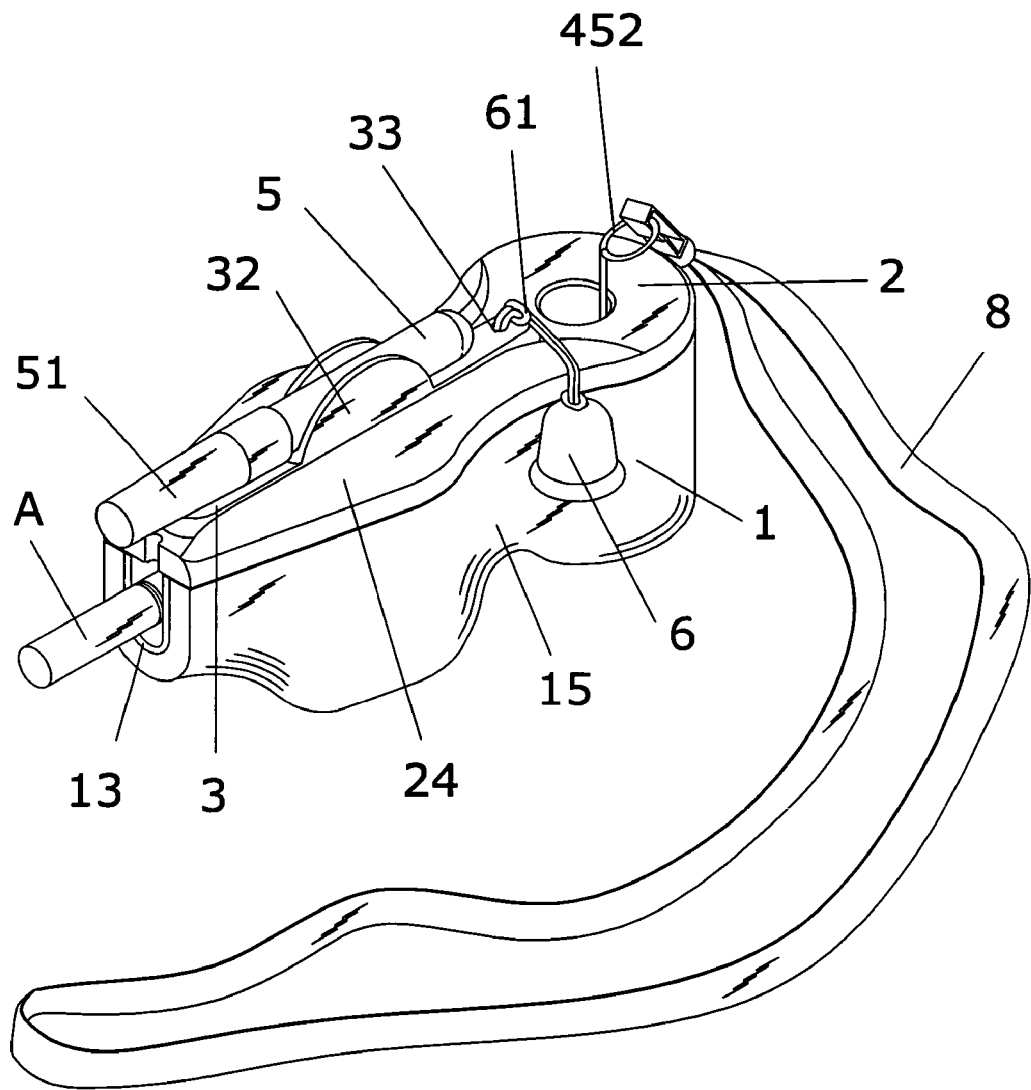
FIG. 9 illustrates the preferred embodiment of the present invention of FIG. 8.

Referring FIGS. 8 and 9, the second preferred embodiment of the present invention is shown. A guarding part 24 is bulged on either opposite side of the air vent 22 of the cover 2 for increasing the solidity of the shield 3 to avoid chapping. And a knotting piece 45 is set on the pivot 4. A tying part 451 is set on one end of the knotting piece 45 for joining the pivot 4 and a buckling part 452 is set on another end of the knotting piece 45 for knotting a sling 8.

About the assembly of this invention, the cylinder 21 of the cover 2 is inserted into the barrel 11 of the trough 1 first. The pivot 4 is penetrated through the spacer 41 into the opening 23 from the hole 14 (unshown). Then, the spacer 41, the elastic band 46, the spacer 41, the elastic washer 42, the nut 44, the knotting piece 45, the spacer 41 and the nut 44 are set sequentially on the end of the pivot 4 in the opening 23 for joining the trough 1 and the cover 2 by fixing the nut 44. The tying part 451 of the knotting piece 45 is set in the opening 23 of the cover 2 and is fixed by a spacer 41 and two nuts 44. And the buckling part 452 of the knotting piece 45 protrudes out of the opening 23 for knotting the sling 8 which a user could use it to carry on.

Obviously the invention is susceptible to changes or alternations without defeating its practicability. Therefore, the preferred embodiment shown in the drawings and described herein is not confined.

What is claimed is:

1. A multi-function portable ashtray comprising:
   a trough having a barrel in one end and a groove near said barrel, said groove having an inserting part in one end and a U-type part in another end;
   a cover having a cylinder for inserting into said barrel of said trough and an air vent;
   a shield having a sticking part for sticking in said air vent of said cover;
   a pivot being set to join said trough and said cover.

2. The multi-function portable ashtray according to claim 1 and further including:
   a holding part is set on either opposite side of said trough.

3. The multi-function portable ashtray according to claim 1 and further including:
   said air vent of said cover laying over said groove for letting air flow into said groove.

4. The multi-function portable ashtray according to claim 1 and further including:
   an opening being set on said cover corresponding to said cylinder for putting a soft plug.

5. The multi-function portable ashtray according to claim 1 and further including:
   a clipping part being set on the opposite end of said shield corresponding said sticking part in order to clamp a brush.

6. The multi-function portable ashtray according to claim 5 and further including:
   a sheath being put on said brush.

7. The multi-function portable ashtray according to claim 1 and further including:
   an aperture being set on one end of said shield for tying an elastic rope,
   said elastic rope being set on said soft plug for blocking said U-type part.

8. The multi-function portable ashtray according to claim 1 and further including:
   a guarding part being set on either opposite side of said air vent of said cover.

9. The multi-function portable ashtray according to claim 1 and further including:
   a knotting piece being set on said pivot.

10. The multi-function portable ashtray according to claim 9 and further including:
   a tying part being set on one end of said knotting piece for joining said pivot;
   a buckling part being set on another end of said knotting piece for knotting a sling.

* * * * *